United States Patent [19]
Koyama et al.

[11] Patent Number: 5,512,528
[45] Date of Patent: Apr. 30, 1996

[54] CATALYSTS USED FOR PRODUCING CARBONIC ACID ESTERS AND METHODS OF PRODUCING CARBONIC ACID ESTERS USING THE SAME

[75] Inventors: Takeshi Koyama; Masao Tonosaki; Nobuhiro Yamada; Kenji Mori, all of Handa, Japan

[73] Assignee: JGC Corporation, Tokyo, Japan

[21] Appl. No.: 215,518

[22] Filed: Mar. 22, 1994

Related U.S. Application Data

[62] Division of Ser. No. 929,294, Aug. 13, 1992, Pat. No. 5,347,031.

[30] Foreign Application Priority Data

Aug. 19, 1991 [JP] Japan ................................. 3-230817
Jun. 29, 1992 [JP] Japan ................................. 4-171331

[51] Int. Cl.⁶ .......................... B01J 21/18; B01J 23/04
[52] U.S. Cl. .................... 502/181; 502/184; 502/225; 502/344
[58] Field of Search ....................... 502/225, 340, 502/344, 345, 181, 183, 184

[56] References Cited

U.S. PATENT DOCUMENTS

| | | | |
|---|---|---|---|
| 4,382,021 | 5/1983 | Laurer et al. | 502/225 |
| 4,451,683 | 5/1984 | Davies et al. | 502/244 |
| 4,503,165 | 3/1985 | Hashiguchi et al. | 502/225 |
| 5,004,827 | 4/1991 | Curnutt. | |
| 5,347,031 | 9/1994 | Koyama et al. | 558/260 |
| 5,387,708 | 2/1995 | Molzahn et al. | 502/164 |

FOREIGN PATENT DOCUMENTS

| | | |
|---|---|---|
| 0038984 | 11/1981 | European Pat. Off.. |
| 0257561 | 3/1988 | European Pat. Off.. |
| 60-144806 | 6/1987 | Japan. |
| 3-16397 | 1/1993 | Japan. |
| 2120117 | 11/1983 | United Kingdom. |
| WO8101284 | 5/1981 | WIPO. |
| 8707601 | 12/1987 | WIPO. |

*Primary Examiner*—Anthony McFarlane
*Attorney, Agent, or Firm*—Darby & Darby

[57] ABSTRACT

The present invention relates to a novel catalyst having a stable catalytic activity for catalyzing the reaction of an alcohol with carbon monoxide and oxygen to produce carbonic acid esters (i.e., carbonate), and also the present invention relates to a method of producing carbonic acid esters using this catalyst. The catalyst of the present invention comprises a copper halide and at least one hydroxide compound selected from a group consisting of alkali metal hydroxides and alkali earth metal hydroxides carried on a porous carrier, and also provide a process of regenerating a catalytic activity of the catalyst.

21 Claims, 2 Drawing Sheets

CATALYSTS USED FOR PRODUCING CARBONIC ACID ESTERS AND METHODS OF PRODUCING CARBONIC ACID ESTERS USING THE SAME

This is a division, of application Ser. No. 07/929,294, filed Aug. 13, 1992, now U.S. Pat. No. 5,347,031.

BACKGROUND OF THE INVENTION

1. Field of the Invention

The present invention relates to a novel catalyst having a stable catalytic activity for catalyzing the reaction of an alcohol with carbon monoxide and oxygen to produce carbonic acid esters (i.e., carbonate) and also relates to a method of producing carbonic acid esters using the catalyst.

2. Prior Art

Carbonic acid esters, such as dimethyl carbonate and the like, have been used as a gasoline extender, an octane number improver, and organic solvents, and also recently used as raw materials instead of phosgene in the process of synthesizing isocyanates and polycarbonates, and various intermediates of agricultural chemicals and medicines.

In the producing carbonic acid esters by oxidation-carbonylation of an alcohol with carbon monoxide (CO) and oxygen ($O_2$) in the presence of catalyst, a copper halide (copper (I)- or copper (II) halide) carried on carrier as a catalyst is known.

For example, International Application Publication WO 87/07601 discloses a process of producing carbonic acid esters by a vapor-phase reaction of an alcohol with carbon monoxide and oxygen in the presence of a catalyst comprising a metal halide or a mixed metal halide impregnated on a carrier, especially, copper (II) chloride, copper (II) chloride/potassium chloride and copper (II) chloride/magnesium chloride impregnated on activated carbon. In using one of these catalysts in the reaction of an alcohol with carbon monoxide and oxygen, however, the conversion of an alcohol and the selectivity to carbonic acid esters are unsatisfactory and a large amount of by-product is yielded. For example, methyl chloride is formed during an initial stage of the reaction and causes metal to corrode. Therefore the conventional catalytic system requires a highly expensive corrosion-resisting reactor vessel.

BRIEF SUMMARY OF THE INVENTION

An object of the invention is to provide a catalyst for producing carbonic acid esters by the reaction including oxidation-carbonylation of an alcohol, comprising a copper halide and at least one hydroxide compound selected from the group consisting of alkali metal hydroxides and alkali earth metal hydroxides carried on a porous carrier.

It is another object of the present invention to provide a process of producing carbonic acid esters by the reaction including oxidation-carbonylation of an alcohol using a catalyst comprising a copper halide and at least one hydroxide compound selected from the group consisting of alkali metal hydroxides and alkali earth metal hydroxides carried on a porous carrier.

It is a further object of the present invention to provide a process for regenerating a catalyst for producing carbonic acid esters by the reaction including oxidation-carbonylation of an alcohol, in which the catalyst comprises a copper halide and at least one hydroxide compound selected from a group consisting of alkali metal hydroxides and alkali earth metal hydroxides carried on a porous carrier and has become deteriorated by use in the reaction of producing carbonic acid esters.

Other and further objects, features and advantages of the invention will appear more fully from the following description.

DESCRIPTION OF THE PREFERRED EMBODIMENT OF THE INVENTION

Figure 1:
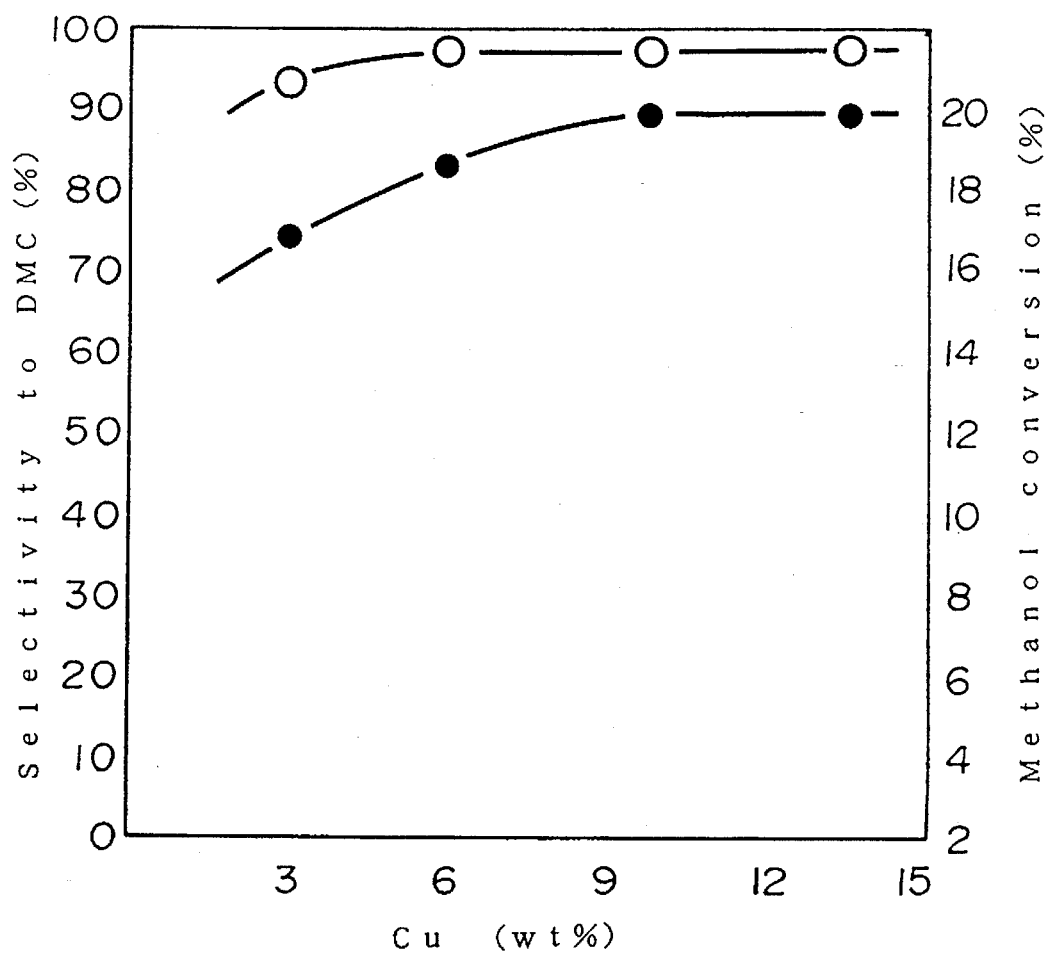
FIG. 1 shows a result of Cu Content of the catalyst with methanol conversion (%) and selectivity (%) to dimethyl carbonate. In the figure, "DMC" means dimethyl carbonate.

Various embodiments of the present invention will now be described.

A catalyst used for producing carbonic acid esters in accordance with the present invention comprises a copper halide and an alkali metal- or an alkali earth metal-hydroxide carried on a porous carrier. Preferably, the alkali metal- or alkali earth metal-hydroxide is carried on the porous carrier in the condition of that a molar ratio of hydroxide group (OH group) of the alkali metal- or alkali earth metal-hydroxide to copper atom in the copper halide is in the range of 0.3 to 2. According to the present invention, the activity of the catalyst will be recovered by contacting the catalyst with a flow of a gas containing a halogen or a hydrogen halide.

The porous carrier used in the present invention is a porous material having a particle diameter of preferably less than or equal to 4.0 mm, more preferably less than or equal to 2.4 mm, and most preferably from 0.02 mm to 1.0 mm. Also, the porous carrier has a surface area of preferably 10 $m^2/g$ or above, and more preferably from 30 to 1000 $m^2/g$.

Further, the above carrier is a porous material selected from a group of activated carbon, titanium oxide, niobium oxide, silica, zirconium oxide, magnesium oxide, alumina, and the like, but activated carbon is more preferable.

The copper halide used in the present invention is selected from a group of mono- or di-valent copper halides such as copper chlorides ($CuCl$, $CuCl_2$), copper bromides ($CuBr$, $CuBr_2$), copper iodides ($CuI$, $CuI_2$), copper fluorides, and mixtures thereof. It is preferable to use copper (II) halide, and also more preferable to use copper (II) chloride.

According to the present invention, the copper halide is prepared as in the form of a solution wherein the copper halide is dissolved in ethanol, methanol, water or the like so as to be easily diffused into the porous carrier. In this case, it is preferable that an amount of the copper halide is in the range of 1.5 to 20 wt %, preferably 5 to 15 wt % as copper per a total weight of the copper halide and the porous carrier. The catalytic activity increases with the increase in CU content, while above the Cu content of about 10 wt %, the catalytic activity remains unchanged.

The alkali metal hydroxide used in the present invention is selected from lithium hydroxide, sodium hydroxide, potassium hydroxide and the like, while the alkali earth metal hydroxide is selected from barium hydroxide and the like. These components are prepared as their aqueous solutions and impregnated in the porous carrier. It is preferable that a molar ratio of hydroxy group of the alkali metal- or the alkali earth metal-hydroxide to copper atom in the copper halide is in the range of 0.3 to 2, more preferably of 0.5 to 1.8, most preferably of 0.8 to 1.5.

In this invention, the porous carrier is filled with the above components using the conventional procedure such as impregnation, blending, co-precipitation or the like. For example, the impregnation is performed as follows: (i) impregnating the porous carrier with the copper (II) halide solution and drying the wet carrier by heating at a temperature of 80°–100° C. under an atmosphere or under an inert gas flow; (ii) impregnating the porous carrier with an alkali metal-hydroxide solution or with an alkali earth metal-hydroxide solution; and (iii) treating the carrier at 80°–400° C. under the atmosphere or under the inert gas flow. In this process, it is allowable to change the order of the two impregnation steps, so that the carrier can be at first impregnated with the alkali metal- or the alkali earth metal-hydroxide solution and then impregnated with the copper (II) halide solution. Optionally, the process is further comprising a step of washing the resulting catalyst impregnated with the above components with distilled water or the like.

In the case of a catalyst of the present invention, a copper halide is reacted with an alkali metal- or an alkali earth metal-hydroxide to form on the carrier a double salt and/or its decomposed compound. In the case of that the catalyst comprising copper (II) halide and NaOH carried on a carrier, for example, $CuCl_2 \cdot 3Cu(OH)_2$ is formed as the double salt and/or a copper oxide chloride of $Cu_2OCl_2$ is formed by a decomposition of $CuCl_2 \cdot 3Cu(OH)_2$.

From the results mentioned below of examples using catalysts A, B, C and the like and a comparative catalyst b, it is obvious that an effect of the present invention is different from one of International Application Publication WO 87/07601 in which an alkali- or an alkali earth metal-halide is impregnated directly on a carrier.

An alcohol used as a reactant of the above process in accordance with the present invention is preferably selected from a group of aliphatic alcohols having 1–6 carbons, cycloaliphatic alcohols having 3–6 carbons and aromatic alcohols, for example, methanol, ethanol, propyl alcohol, butanol, pentanol, hexanol, cyclopropanol, cyclobutanol, cyclohexanol, benzyl alcohol or mixtures thereof. It is more preferable to use a monovalent alcohol such as methanol, ethanol or the like. According to the present invention, symmetrical carbonic acid diesters are produced when one type of the above alcohols is used, while a mixture of symmetrical and unsymmetrical carbonic acid diesters is produced when a mixture of the alcohols is used.

A reaction temperature for producing carbonic acid esters by the vapor-phase reaction of an alcohol with carbon monoxide and oxygen is in the range of 70° to 350° C., preferably 80° to 250° C., and more preferably 100° to 200° C. In this case, the vapor-phase reaction is performed at an atmospheric pressure or at a pressure up to 35 kg/cm²G, preferably at 2 to 20 kg/cm²G, and more preferably at 5 to 15 kg/cm²G.

A molar ratio of carbon monoxide to an alcohol (CO/alcohol molar ratio) is in the range of 0.01 to 100, preferably 0.5 to 20, and more preferably 1 to 10, while a molar ratio of the oxygen to an alcohol ($O_2$/alcohol molar ratio) is in the range of 0.01 to 2.0, preferably 0.05 to 1.0, and more preferably 0.05 to 0.5. Also, a molar ratio of carbon monoxide to oxygen (CO/$O_2$ molar ratio) is in the range of 1 to 1000, preferably 10 to 100, and more preferably 20 to 50.

Oxygen used in the present invention is supplied to the reaction vessel in the form of a pure molecular oxygen ($O_2$), or followed by diluting oxygen with an inert gas such as nitrogen, argon or the like.

The vapor-phase reaction mentioned above is a fixed or fluidized bed type, but not limited to these types.

In accordance with the present invention, following carbonic acid esters can be produced: dimethyl carbonate; diethyl carbonate; dipropyl carbonate; dibutyl carbonate; dipenthyl carbonate; dihexyl carbonate; dicyclopropyl carbonate; dicyclobutyl carbonate; dicyclopenthyl carbonate; dicyclohexyl carbonate; dibenzyl carbonate; methylethyl carbonate; methylpropyl carbonate; ethylpropyl carbonate; and the like.

When the activity of the catalyst decreases, the catalytic activity can be recovered by contacting the catalyst with a gas containing a halogen, a hydrogen halide, an aqueous solution thereof, or an organic halide compound which generates a halogen or a hydrogen halide in the recovering process. In this case, the halogen is selected from a group of chlorine, fluorine, bromine and the like, while the hydrogen halide is selected from hydrogen fluoride, hydrogen chloride, hydrogen bromide and the like. The recovering process can be performed at 150°–300° C., preferably, 150°–250° C. and for a time of 0.5 hours or above, preferably, 0.5–3 hours. It is preferable to carry out the recovering process under a flow of an inert gas such as nitrogen, helium, argon or the like, or under a flow of a reducing gas such as hydrogen, carbon monoxide or the like. It is also preferable that an amount of the halogen or the hydrogen halide is in the range of 0.1 to 10 volume % when the recovering process is performed in the presence of the inert gas or the reducing gas.

In general, the recovering process has two steps, i.e., a fist step of heating the catalyst up to an appropriate temperature under an inert or reducing atmosphere and a second step of contacting the catalyst with a gas containing a halogen or a hydrogen halide at an appropriate temperature and an appropriate flow rate under an inert, a reducing atmosphere and like for a predetermined reaction time.

EXAMPLE 1

A copper (II) chloride solution was prepared by dissolving 12.9 g of copper (II) chloride in 100 ml of ethanol; and a sodium hydroxide solution was prepared by dissolving 3.8 g of sodium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The cooled particles were further impregnated with 8 ml of the sodium hydroxide solution. After the second impregnation, the particles were subjected to a thermal treating (100° C., 3 hours) under a flow of nitrogen gas to obtain catalyst A (Cu content=3 wt %, OH/Cu molar ratio= 1.0).

The Cu content was calculated by the following formula:

Cu content (wt %)

=[a weight of Cu in the copper halide/(a weight of the copper halide+a weight of the carrier)]×100

The activity experiment was done by using a fixed bed reactor comprising a stainless tube of 12 mm inner-diameter.

The tube was filled with 7 ml of the catalyst A, and then a catalytic reaction was done by introducing methanol, carbon monoxide, and oxygen into the reactor at the flow rates of 5 g/hr., 57.8 ml/min., and 3.6 ml/min., respectively, under the vapor phase reaction conditions of 6 kg/cm²G and 130° C. The result after 2 hours from the start of reaction was shown in Table 1.

In the table, the conversion (X) of the alcohol and the selectivity (Y) to the carbonic acid ester were calculated by the following formula.

$X=(A_0-A)/A_0 \times 100$ (%), $Y=B/(A_0-A) \times 100$ (%)

wherein "$A_0$" means an initial amount of the alcohol (moles) provided as a reactant, "A" means an amount of the unreacted alcohol (moles), and "B" means an amount of the alcohol converted to the carbonate (moles).

EXAMPLE 2

The catalyst A prepared by the same way as that of example 1 was washed with 200 ml of distilled water for 1 hour, and then dried by introducing an inert gas (nitrogen) at 100° C. for 3 hours to obtain catalyst B (Cu content = 3 wt %, OH/Cu molar ratio=1.0).

The activity of catalyst B was evaluated in the same way as that of example 1 and the results were listed in Table 1.

EXAMPLE 3

The copper (II) chloride solution was prepared by the same way as that of example 1, while a potassium hydroxide solution was prepared by dissolving 5.3 g of potassium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The cooled particles were further impregnated with 8 ml of the potassium hydroxide solution. After the second impregnation, the particles were subjected to a thermal treating (100° C., 3 hours) under a flow of nitrogen gas to obtain catalyst C (Cu content=3 wt %, OH/Cu molar ratio=1.0).

The activity of the catalyst C was evaluated in the same way as described in example 1 and the results were listed in Table 1.

EXAMPLE 4

The copper (II) chloride solution was prepared by the same way as that of example 1, while a lithium hydroxide solution was prepared by dissolving 2.4 9 of lithium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The cooled particles were further impregnated with 8 ml of the lithium hydroxide solution. After the second impregnation, the particles were subjected to a thermal treating (100° C., 3 hours) under a flow of nitrogen gas to obtain catalyst D (Cu content=3 wt %, OH/Cu molar ratio= 1.0).

The activity of catalyst D was evaluated in the same way as that of example 1 and the results were listed in Table 1.

EXAMPLE 5

The copper (II) chloride solution was prepared by the same way as that of example 1, while a barium hydroxide solution was prepared by dissolving 8.3 g of barium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The cooled particles were further impregnated with 8 ml of the barium hydroxide solution. After the second impregnation, the particles were subjected to a thermal treating (100° C., 3 hours) under a flow of nitrogen gas to obtain catalyst E (Cu content=3 wt % Cu, OH/Cu molar ratio 1.0).

The activity of catalyst E was evaluated in the same way as that of example 1 and the results were listed in Table 1.

EXAMPLE 6

A copper (II) chloride solution was prepared by the same way as that of example 1, while a sodium hydroxide solution was prepared by dissolving 7.68 g of sodium hydroxide in 100 ml of distilled water.

Activated carbon particles (15 g) were impregnated with 8 ml of the copper (II) chloride solution, followed by drying under a flow of nitrogen gas at 100° C. for 3 hours. Then, the dried particles were cooled down to a room temperature. The above steps of the impregnation were repeated once more, and then the cooled particles were further impregnated with 8 ml of the sodium hydroxide solution. After the impregnation, the particles were subjected to a thermal treating (100° C., 3 hours) under a flow of nitrogen gas to obtain catalyst F (Cu content=6 wt %, OH/Cu molar ratio=1.0).

The activity of catalyst F was evaluated in the same way as that of example 1 and the results were listed in Table 1.

EXAMPLE 7

The copper (II) chloride solution was prepared by dissolving 25 g of copper (II) chloride in 100 ml of ethanol and a sodium hydroxide solution was prepared by dissolving 14.8 g of sodium hydroxide in 100 ml of distilled water.

Activated carbon particles (15 g) were impregnated with 8 ml of the copper (II) chloride solution, followed by drying under a flow of nitrogen gas at 100° C. for 3 hours. Then, the dried particles were cooled down to a room temperature. The above steps of the impregnation were repeated once more, and then the cooled particles were further impregnated with 8 ml of the sodium hydroxide solution. After the impregnation, the particles were subjected to a thermal treating (100° C., 3 hours) under a flow of nitrogen gas to obtain catalyst G (Cu content=9.9 wt %, OH/Cu molar ratio=1.0).

The activity of catalyst G was evaluated in the same way as that of example 1 and the results were listed in Table 1.

EXAMPLE 8

The copper (II) chloride solution was prepared by the same way as that of example 7, while a sodium hydroxide solution was prepared by dissolving 22.3 g of sodium hydroxide in 100 ml of distilled water.

Activated carbon particles (15 g) were impregnated with 8 ml of the copper (II) chloride solution, followed by the drying under a flow of nitrogen gas at a temperature of 100° C. for 3 hours. Then, the dried particles were cooled down to a room temperature. The above steps of the impregnation were repeated twice and then the cooled particles were further impregnated with 8 ml of the sodium hydroxide solution. After the impregnation, the particles were subjected to a thermal treating (100° C., 3 hours) under a flow of nitrogen gas to obtain catalyst H (Cu content = 13.5 wt %, OH/Cu molar ratio=1.0).

The activity of catalyst H was evaluated in the same way as that of example 1 and the results were listed in Tables 1, 2 and 3.

EXAMPLE 9

The copper (II) chloride solution was prepared by the same way as that of example 1, while a sodium hydroxide solution was prepared by dissolving 1.92 g of sodium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The cooled particles were further impregnated with 8 ml of the sodium hydroxide solution. After the second impregnation, the particles were subjected to a thermal treating (100° C., 3 hours) under a flow of nitrogen gas to obtain the catalyst I (Cu content=3 wt %, OH/Cu molar ratio=0.5).

The activity of catalyst I was evaluated in the same way as that of example 1 and the results were listed in Table 1.

EXAMPLE 10

The copper (II) chloride solution was prepared by the same way as that of example 1, while a sodium hydroxide solution was prepared by dissolving 5.75 9 of sodium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The cooled particles were further impregnated with 8 ml of the sodium hydroxide solution- After the second impregnation, the particles were subjected to a thermal treating (100° C., 3 hours) under a flow of nitrogen gas to obtain catalyst J (Cu content=3 wt %, OH/Cu molar ratio=1.5).

The activity of catalyst J was evaluated in the same way as that of example 1 and the results were listed in Table 1.

EXAMPLE 11

The copper (II) chloride solution was prepared in the same way as that of example 1, while a sodium hydroxide solution was prepared by dissolving 7.68 g of sodium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The cooled particles were further impregnated with 8 ml of the sodium hydroxide solution. After the second impregnation, the particles were subjected to a thermal treating (100° C., 3 hours) under a flow of nitrogen gas to obtain catalyst K (Cu content=3 wt %, OH/Cu molar ratio= 2).

The activity of catalyst K was evaluated in the same way as that of example 1 and the results were listed in Table 1.

EXAMPLE 12

The copper (II) chloride solution was prepared by the same way as that of example 8 and a sodium hydroxide solution was prepared by the same way as that of example 8.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The above steps of impregnation were repeated twice and then the cooled particles were further impregnated with 8 ml of the sodium hydroxide solution. After the impregnation, the particles were subjected to a thermal treating (150° C., 3 hours) under a flow of nitrogen gas to obtain catalyst L (Cu content=13.5 wt %, OH/Cu molar ratio=1.0).

The activity of catalyst L was evaluated in the same way as that of example 1 and the results were listed in Tables 1 and 3.

EXAMPLE 13

The preparation of solutions and the impregnation method of the copper (II) chloride and the sodium hydroxide solution were done by the same way as that of example 12.

After the impregnation of the sodium hydroxide solution, the particles were subjected to a thermal treating (300° C., 3 hours) under a flow of nitrogen gas to obtain catalyst M (Cu content=13.5 wt %, OH/Cu molar ratio=1.0).

The activity of catalyst M was evaluated in the same way as that of example 1 and the results were listed in Tables 1 and 3.

EXAMPLE 14

A copper (II) chloride solution was prepared by dissolving 25 g of copper (II) chloride in 100 ml of distilled water; and a sodium hydroxide solution was prepared by the same way as that of example 8.

Activated carbon particles (15 g) were impregnated with 8 ml of the copper (II) chloride solution, followed by the drying under a flow of nitrogen gas at 100° C. for 3 hours. After that, the dried particles were cooled down to a room temperature. The above steps of the impregnation were repeated twice, and then the cooled particles were further impregnated with 8 ml of the sodium hydroxide solution. After the impregnation, the particles were subjected to a thermal treating (300° C., 3 hours) under a flow of nitrogen gas to obtain catalyst N (Cu content=13.5 wt %, OH/Cu molar ratio=1.0).

The activity of catalyst N was evaluated in the same way as that of example 1 and the results were listed in Tables 1 and 3.

EXAMPLE 15

10 ml of the catalyst H was washed with 200 ml of distilled water for 1 hour and then dried by introducing a flow of nitrogen gas at 100° C. for 3 hours to obtain catalyst O (Cu content=13.5 wt %, OH/Cu molar ratio=1.0).

The activity of catalysts O was evaluated in the same way as that of example 1, except of that the evaluations were performed after 2 and 50 hours from the initiation. The results obtained were listed in Tables 1 and 2.

EXAMPLE 16

10 ml of catalyst I was washed with 200 ml of distilled water for 1 hour and then dried by introducing a flow of nitrogen at 100° C. for 3 hours to obtain catalyst P (Cu content=3 wt %, OH/Cu molar ratio=0.5).

The activity of the catalyst P was estimated in the same way as that of example 1 and the results were listed in Table 1.

EXAMPLE 17

A copper (II) chloride solution was prepared by the same way as that of example 7, and a sodium hydroxide solution was prepared by dissolving 11.15 g of sodium hydroxide in 100 ml of distilled water.

Activated carbon particles (15 g) were impregnated with 8 ml of the copper (II) chloride solution, followed by the drying under a flow of nitrogen gas at 100° C. for 3 hours. Then, the dried particles were cooled down to a room temperature. The above steps of the impregnation were repeated twice and then the cooled particles were further impregnated with 8 ml of the sodium hydroxide solution. After the impregnation, the particles were subjected to a thermal treating (100° C., 3 hours) under a flow of nitrogen gas to obtain catalyst Q (cu content=13.5 wt %, OH/Cu molar ratio=0.5).

The activity of catalyst Q were evaluated in the same way as that of example 1 and the results were listed in Table 1.

EXAMPLE 18

The catalyst Q (10 ml) was washed with 200 ml of distilled water for 1 hour and then dried by introducing a flow of nitrogen gas at 100° C. for 3 hours to obtain catalyst R (Cu content=13.5 wt %, OH/Cu molar ratio=0.5).

The activity of catalyst R was evaluated in the same way as that of example 1 and the results were listed in Table 1.

EXAMPLE 19

A copper (II) bromide solution was prepared by dissolving 21.9 g of copper (II) bromide in 100 ml of distilled water, and also a sodium hydroxide solution was prepared by dissolving 3.9 g of sodium hydroxide in 100 ml of distilled water.

Activated carbon particles (15 g) were impregnated with 8 ml of the copper (II) bromide solution, followed by the drying under a flow of nitrogen gas at 100° C. for 3 hours. Then, the dried particles were cooled down to a room temperature. The cooled particles were further impregnated with 8 ml of the sodium hydroxide solution. After the second impregnation, the particles were subjected to a thermal treating (100° C., 3 hours) under a flow of nitrogen gas to obtain catalyst S (Cu content=3 wt %, OH/Cu molar ratio=1).

The activity of the catalyst S was evaluated in the same way as that of example 1 and the results were listed in Table 1.

EXAMPLE 20

A copper (II) chloride solution was prepared by dissolving 25.0 g of copper (II) chloride in 100 ml of distilled water, and also a sodium hydroxide solution was prepared by dissolving 22.3 g of sodium hydroxide in 100 ml of distilled water.

Activated carbon particles (15 g) having a diameter in the range of 2.8 to 4.0, 1.7 to 2.4, 1.0 to 1.7, 0.7 to 1.0, 0.7 to 0.75 or 0.3 to 0.35 mm, respectively, were impregnated with 8 ml of the copper (II) chloride solution, followed by drying under a flow of nitrogen gas at 100° C. for 3 hours. After that, the dried particles were cooled down to a room temperature. The same steps were repeated twice, and then the cooled particles were further impregnated with 8 ml of the sodium hydroxide solution. After the impregnation, the particles were subjected to a thermal treating (100° C., 3 hours) under a flow of nitrogen gas to obtain the catalyst (Cu content=13.5 wt %, OH/Cu molar ratio=1).

The activity experiment was done by using a fixed bed reactor comprising a stainless tube of 12 mm inner-diameter.

The tube was filled with 7 ml of the catalyst, and then a catalytic reaction was done by introducing methanol, carbon monoxide, and oxygen into the reactor at the flow rates of 5 g/hr., 57.8 ml/min., and 3.6 ml/min., respectively, under the vapor phase reaction conditions of 6 kg/cm$^2$G and 130° C. After 2, 50, and 100 hours from the initiation, the activity of the catalyst was evaluated, respectively- The results were listed in Table 4.

EXAMPLE 21

The activity of catalyst A was decreased to 60% compared with that of a fresh one due to the use in the reaction of methanol with carbonic monoxide and oxygen to produce dimethyl carbonate.

7 ml of the sample (used catalyst A) was heated up to 250° C. under a flow of inert gas (nitrogen), and then the sample was treated by a flow of hydrogen (0.3 Nl/hour) and 3.6% hydrochloric acid (1.2 ml/hour) at 250° C. for 3 hours to regenerate the catalyst A.

The activity of the regenerated catalyst A-1 was evaluated by the same way as described in the example 1. After 2 hours from the initiation, methanol conversion was 16.4% and selectivity to dimethyl carbonate was 92%. The catalytic activity of the regenerated catalyst A-1 was similar with that of the fresh catalyst A.

EXAMPLE 22

The regenerating process was performed by the same way as that of example 21, except that a flow of inert gas (nitrogen) (0.3 Nl/hour) was used instead of the hydrogen.

The activity of the regenerated catalyst A-2 was evaluated by the same way as described in the example 1. After 2 hours from the initiation, methanol conversion was 16.5% and selectivity to dimethyl carbonate was 93%. The catalytic activity of the regenerated catalyst A-2 was similar with that of the fresh catalyst A.

EXAMPLE 23

The activity of catalyst A was decreased to 60% compared with that of a fresh one due to the use in the reaction.

7 ml of the sample (used catalyst A) was heated up to 250° C. under a flow of inert gas (nitrogen), and then the sample was treated by a flow of 2% HCl-N$_2$ gas (160 ml/1 ml catalyst/hour) at a standard condition (15° C., 1 atm) for 7 hours to regenerate the catalyst A.

The activity of the regenerated catalyst A-3 was evaluated by the same way as described in the example 1. After 2 hours from the initiation, methanol conversion was 16.7% and selectivity to dimethyl carbonate was 93%. The catalytic activity of the regenerated catalyst A-3 was similar with that of the fresh catalyst A.

EXAMPLE 24

The regenerating process by the same way as that of example 23 was performed, except that a flow of 5% $Cl_2$-$N_2$ gas (100 ml/1 m catalyst/hour) was used instead of 2% HCl-$N_2$ gas.

The activity of the regenerated catalyst A-4 was evaluated by the same way as described in the example 1. After 2 hours from the initiation, methanol conversion was 16.6% and selectivity to dimethyl carbonate was 93%. The catalytic activity of the regenerated catalyst A-4 was similar with that of the fresh catalyst A.

COMPARATIVE EXAMPLE 1

Activated carbon particles (15 g) were impregnated with 8 ml of the copper (II) chloride solution of example 1, followed by the drying under a flow of nitrogen gas at 100° C. for 3 hours. After that, the dried particles were cooled down to a room temperature to obtain catalyst a (Cu content=3 wt %, OH/Cu molar ratio=0).

The activity of catalyst a was evaluated in the same way as that of example 1 and the results were listed in Table 1.

COMPARATIVE EXAMPLE 2

Activated carbon particles (15 g) were impregnated with 8 ml of the copper (II) chloride solution of example 1, followed by the drying under a flow of nitrogen gas at 100° C. for 3 hours. After that, the dried particles were cooled down to a room temperature. Then the cooled particles were further impregnated with 8 ml of a potassium chloride solution (7.15 g of potassium chloride dissolved in 100 ml of distilled water). After the second impregnation, the particles were subjected to a thermal treating (100° C., 3 hours) under a flow of nitrogen gas to obtain catalyst b (Cu content=3 wt %, OH/Cu molar ratio=0).

The activity of catalyst b was evaluated in the same way as that of example 1 and the results were listed in Table 1.

COMPARATIVE EXAMPLE 3

Activated carbon particles (15 g) were impregnated with 8 ml of the copper (II) bromide solution of the example 19, followed by the drying under a flow of nitrogen gas at 100° C. for 3 hours. After that, the dried particles were cooled down to a room temperature to obtain catalyst c (Cu content=3 wt %, OH/Cu molar ratio=0).

The activity of catalyst c was evaluated in the same way as that of example 1 and the results were listed in Table 1.

The results obtained from the above examples were listed in the following tables.

TABLE 1

Catalytic activities of catalysts A–S and a–c.

| Exp. No. | Catalyst | Cu-content (wt %) | MOH or M(OH)$_2$ | OH/Cu | Conv. (%) | Select. (%) |
|---|---|---|---|---|---|---|
| 1 | A | 3 | NaOH | 1 | 16.7 | 93 |
| 2 | B | 3 | NaOH | 1 | 14.0 | 91 |
| 3 | C | 3 | KOH | 1 | 18.3 | 94 |
| 4 | D | 3 | LiOH | 1 | 16.0 | 91 |
| 5 | E | 3 | Ba(OH)$_2$ | 1 | 16.8 | 91 |
| 6 | F | 6 | NaOH | 1 | 18.5 | 97 |
| 7 | G | 9.9 | NaOH | 1 | 19.8 | 97 |
| 8 | H | 13.5 | NaOH | 1 | 19.8 | 97 |
| 9 | I | 3 | NaOH | 0.5 | 9.5 | 82 |
| 10 | J | 3 | NaOH | 1.5 | 16.6 | 93 |
| 11 | K | 3 | NaOH | 2 | 4.9 | 57 |
| 12 | L | 13.5 | NaOH | 1 | 21.1 | 97 |
| 13 | M | 13.5 | NaOH | 1 | 23.0 | 97 |
| 14 | N | 13.5 | NaOH | 1 | 23.0 | 97 |
| 15 | O | 13.5 | NaOH | 1 | 19.7 | 97 |
| 16 | P | 3* | NaOH | 0.5 | 8.4 | 88 |
| 17 | Q | 13.5 | NaOH | 0.5 | 14.0 | 87 |
| 18 | R | 13.5* | NaOH | 0.5 | 13.0 | 92 |
| 19 | S | 3 | NaOH | 1 | 13.0 | 81 |
| Comp. Exp. No. | | | | | | |
| 1 | a | 3 | — | 0 | 4.0 | 52 |
| 2 | b | 3 | KCl | 0 | 4.5 | 58 |
| 3 | c | 3 | — | 0 | 4.1 | 49 |

M: alkyl metal or alkyl earth metal
Conv.: methanol conversion (%)
Select.: selectivity to dimethyl carbonate (%)
*: Cu-content before washing

TABLE 2

Catalytic activities of catalysts H and O after 2 and 50 hours from the initiation.

| Exp. No. | Catalyst | after 2 hours | | after 50 hours | |
|---|---|---|---|---|---|
| | | Conv. | Select. | Conv. | Select. |
| 8 | H | 19.8 | 97 | 14.3 | 94 |
| 15 | O | 19.7 | 97 | 14.6 | 94 |

TABLE 2-continued

Catalytic activities of catalysts H and O after 2 and 50 hours from the initiation.

| Exp. No. | Catalyst | after 2 hours | | after 50 hours | |
| --- | --- | --- | --- | --- | --- |
| | | Conv. | Select. | Conv. | Select. |

Conv.: methanol conversion (%)
Select.: selectivity to dimethyl carbonate (%)

TABLE 3

Effects of the thermal treatment on catalytic activities of catalysts H and L–N.

| Exp. No. | Catalyst | a temp. of thermal treatment (°C.) | Conv. | Select. |
| --- | --- | --- | --- | --- |
| 8 | H | 100 | 19.8 | 97 |
| 12 | L | 150 | 21.1 | 97 |
| 13 | M | 300 | 23.0 | 97 |
| 14 | N | 300 | 23.0 | 97 |

Conv.: methanol conversion (%)
Select.: selectivity to dimethyl carbonate (%)

TABLE 4

Effects of the particle size on catalytic activities of catalysts after 3, 50 and 100 hours from the initiation.

| Catalyst size | after 3 hours | | after 50 hours | | after 100 hours | |
| --- | --- | --- | --- | --- | --- | --- |
| | Conv. | Select. | Conv. | Select. | Conv. | Select. |
| 2.8–4.0 | 14.0 | 96.0 | 10.2 | 94.4 | 6.8 | 92.7 |
| 1.7–2.4 | 14.2 | 96.3 | 10.0 | 94.0 | 6.3 | 92.4 |
| 1.0–1.7 | 14.2 | 96.3 | 11.0 | 94.3 | 7.3 | 92.5 |
| 0.7–1.0 | 14.8 | 96.5 | 14.8 | 95.8 | 12.6 | 95.7 |
| 0.7–0.75 | 14.6 | 96.5 | 14.4 | 95.9 | 13.8 | 95.7 |
| 0.3–0.35 | 14.8 | 96.6 | 14.5 | 96.2 | 13.9 | 95.7 | catalyst size: a particle diameter of the activated carbon (mm)
Conv.: methanol conversion (%)
Select.: selectivity to dimethyl carbonate (%)

According to table 1, the catalysts of the examples 1–19 comprising a copper halide and an alkali metal- or an alkali earth metal-hydroxide impregnated on porous carrier are more active than that of the comparative examples with respect to the methanol conversion (%) and the selectivity (%) to the dimethyl carbonate.

Figure 2:
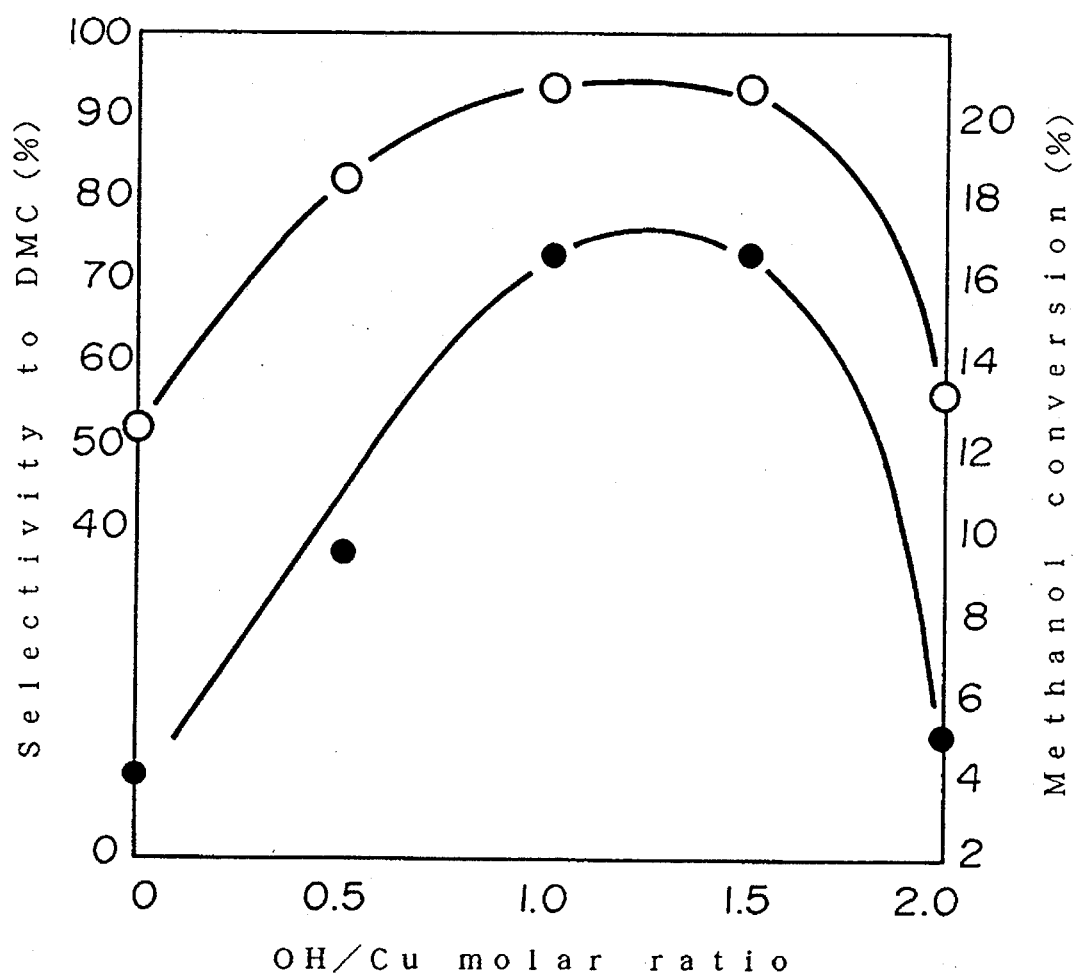
FIG. 2 shows a relationship between OH/Cu molar ratio and methanol conversion and selectivity to dimethyl carbonate.

FIG. 2 indicates an effect of a molar ratio (OH/Cu molar ratio) of hydroxy group of the alkali metal- and the alkali earth metal-hydroxide to copper atom in the copper halide. In this figure, the results obtained by examples 1, 9, 10 and 11 and comparative examples 1 were plotted. As shown in the figure, the methanol conversion (%) (—●—) and the selectivity (%) to the dimethyl carbonate (—O—) are improved when the OH/Cu molar ratio is in the range of 0.3 to 2, preferably 0.5 to 1.8. In addition, their maximum values are obtained when the OH/Cu molar ratio is in the range of 1.0–1.5.

It is noted that the catalyst B shows not only almost the same activity as compared with the catalyst A but also a higher activity compared with the catalyst b comprising KCl of the comparative example 2 in spite of that the catalyst B is prepared by washing the catalyst A with distilled water for 1 hour so as to eliminate water-soluble components such as NaCl which may be produced by reacting NaOH with $CuCl_2$.

Consequently, an amount of NaCl impregnated in the carrier cannot be an important factor for improving the methanol conversion and the selectivity to dimethyl carbonate.

Furthermore, the results shown in table 2 supports the idea that NaCl are not an important factor for keeping the methanol conversion and the selectivity to dimethyl carbonate to the constant state.

FIG. 1 shows an effect of the Cu-content of the catalyst. In this figure, the results obtained by the examples 1, 6, 7 and 8 are plotted and these results make curves which slope to the left of the figure. The catalytic activity increases with the increase in Cu content of the catalyst. On the other hand, when the Cu-content is higher than about 10 wt %, the methanol conversion (—●—) and the selectivity to dimethyl carbonate (—O—) become a constant.

Further, it is noted that the reaction vessel is readily corroded during the reaction in the presence of catalyst a, b or c. On the other hand, we could not find any defects caused by corrosion during the reaction in the presence of the catalysts of the present invention.

As shown in Table 4, the particle diameter of the catalyst is one of the important factors for obtaining a high activity. Consequently, a particle diameter of the porous catalyst is preferably less than or equal to 4.0 mm, more preferably less than or equal to 2.4 mm, and most preferably from 0.02 to 1.0 mm. The catalyst comprising the particle size of over 1.0 mm diameter gradually losses its catalytic activity with the reaction time.

Accordingly, catalysts in accordance with the present invention show their high catalytic activities (i.e., the high conversion of an alcohol and the high selectivity to carbonates) in the reaction for producing carbonates. In accordance with the present invention, there is no need to protect a surface of the reactor from severely corrosive conditions because a generation of undesirable products such as a corrosive component can be avoided by using the catalyst of the present invention.

From the results of the examples 21–24, furthermore, the activity of the catalyst according to the present invention can be easily recovered.

It should also be understood that the foregoing relates to only a preferred embodiment of the invention, and that it is intended to cover all changes and modifications of the example of the present invention herein chosen for the purpose of the disclosure, which do not constitute departures from the spirit of the invention.

What is claimed is:

1. A catalyst for producing carbonic acid esters by the reaction including oxidation-carbonylation of an alcohol, comprising a copper halide and at least one hydroxide compound selected from the group consisting of alkali metal hydroxides and alkali earth metal hydroxides carried on a porous carrier, Wherein a molar ratio of hydroxide group of the hydroxide compound to copper atom in the Copper halide is in the range of 0.3 to 2.0.

2. A catalyst in accordance with claim 1, wherein the copper halide is copper (II) halide.

3. A catalyst in accordance with claim 1, wherein the porous carrier is activated carbon.

4. A catalyst in accordance with claim 1, wherein an amount of the copper halide is in the range of 1.5 to 20 wt % as Cu per a total weight of the copper halide and the porous carrier.

5. A catalyst in accordance with claim 1, wherein an amount of copper halide is within the range of 3 to 15 wt % as Cu per the total weight of the copper halide and the porous carrier.

6. A catalyst in accordance with claim 1, wherein a particle diameter of the catalyst is less than or equal to 4.0 min.

7. A catalyst in accordance with claim 1, wherein a particle diameter of the catalyst is within the range of 0.02 to 1.0 mm.

8. A catalyst in accordance with claim 1, wherein the molar ratio of the hydroxide group of the hydroxide compound to copper atom in the copper halide is within the range of 0.5 to 1.8.

9. A catalyst in accordance with claim 1, wherein the molar ratio of the hydroxide group of the hydroxide compound to copper atom in the copper halide is within the range of 0.8 to 1.5.

10. A catalyst in accordance with claim 1, wherein the copper halide is a copper bromide or a copper chloride.

11. A catalyst in accordance with claim 1, wherein the hydroxide compound is selected from a group consisting of sodium hydroxide, potassium hydroxide, lithium hydroxide and barium hydroxide.

12. A catalyst for producing carbonic acid esters by the reaction including oxidation-carbonylation of an alcohol, comprising a copper halide and at least one hydroxide compound selected from the group consisting of alkali metal hydroxides and alkali earth metal hydroxides carried on a porous carrier;

wherein the copper halide is a copper bromide or a copper chloride, the hydroxide compound is selected from a group consisting of sodium hydroxide, potassium hydroxide, lithium hydroxide and barium hydroxide;

a molar ratio of hydroxide group of the hydroxide compound to copper atom in the copper halide is within the range of 0.3 to 2.0; and an amount of the copper halide is within the range of 1.5 to 20 wt % as Cu per total weight of the copper halide plus the porous carrier.

13. A catalyst in accordance with claim 12, wherein the molar ratio of the hydroxide group of the hydroxide compound to copper atom in the copper halide is within the range of 0.5 to 1.8.

14. A catalyst in accordance with claim 13, wherein the copper halide is copper (II) halide.

15. A catalyst in accordance with claim 14, wherein the porous carrier is activated carbon.

16. A catalyst in accordance with claim 15, wherein a particle diameter of the catalyst is less than or equal to 4.0 mm.

17. A catalyst in accordance with claim 14, wherein a particle diameter of the catalyst is within the range of 0.02 to 1.0 min.

18. A catalyst for producing carbonic acid esters by the reaction including oxidation-carbonylation of an alcohol, which comprises a copper oxide halide carried on a porous carrier.

19. A catalyst in accordance with claim 18, wherein the copper oxide halide is specified by the formula $CU_2OX_2$, wherein X is a halogen.

20. A catalyst in accordance with claim 18, wherein the copper oxide halide is selected from a group consisting of a copper oxide chloride and a copper oxide bromide.

21. A catalyst in accordance with claim 18, wherein the porous carrier is activated carbon.

\* \* \* \* \*